United States Patent [19]

LeBoeuf et al.

[11] 4,022,204

[45] May 10, 1977

[54] DIMENSIONALLY STABLE SHAPED EYE BANDAGES

[75] Inventors: Albert R. LeBoeuf, Sturbridge; William R. Grovesteen, West Dudley, both of Mass.

[73] Assignee: Warner-Lambert Company, Morris Plains, N.J.

[22] Filed: Mar. 1, 1976

[21] Appl. No.: 662,765

Related U.S. Application Data

[62] Division of Ser. No. 526,022, Nov. 21, 1974, Pat. No. 3,978,164.

[52] U.S. Cl. .............................. 128/163; 128/155
[51] Int. Cl.$^2$ ..................................... A61F 13/12
[58] Field of Search ............... 128/155, 156, 132 R, 128/163, 76

[56] References Cited

UNITED STATES PATENTS

| | | | |
|---|---|---|---|
| 3,092,103 | 6/1963 | Mower | 128/132 R |
| 3,952,735 | 4/1976 | Wirtschafter et al. | 128/163 |
| 3,973,561 | 8/1976 | Kane | 128/163 |
| 3,978,164 | 8/1976 | Le Boeuf et al. | 260/885 |

*Primary Examiner*—John D. Yasko
*Attorney, Agent, or Firm*—Albert H. Graddis; Frank S. Chow; Anne M. Kelly

[57] ABSTRACT

A dimensionally stable, shaped eye bandage for medicament delivery comprises polymerized random graft copolymers containing (in the dry state) from 67.2% to 79.3% HEMA; from 14.25% to 35% PVP; from 0.1% to 4.04% EDMA; from 0.1% to 2.5% MA; from 0.1% to 5.0% water; from 0 to 4 ppm HQ inhibitor; and from 50 to 250 ppm MEHQ inhibitor. The eye bandage composition contains from 45% to 65% water after hydration. An improved method for shaping, polymerizing, and cutting and hydrating the eye bandage composition is provided. The polymerization is conducted using only a low temperature initiator, by de-gassing prior to polymerization to remove substantially all oxygen, and by conducting the initial polymerization reaction at from 23° C to 30° C for 16 to 30 hours, during which the heat of the reaction is continuously absorbed to control the reaction exotherm. A closed, rod-shaped casting mold, lined with a polyester film material, is used and the polymeric rod obtained may be cut, machined and polished to obtain the shaped eye bandage. Thereafter, hydration is conducted in a buffered, 0.85% to 0.9% saline solution, at a pH of 7.0 to 7.1.

5 Claims, No Drawings

DIMENSIONALLY STABLE SHAPED EYE BANDAGES

This is a division of application Ser. No. 526,022 filed Nov. 21, 1974, now U.S. Pat. No. 3,978,164.

BACKGROUND OF THE INVENTION

1. Field of the Invention

The present invention relates to a dimensionally stable, shaped eye bandage composition obtained by carefully controlling the formulation ingredients, the polymerization processes, and molding techniques. The polymerized product obtained is subjected to cutting and polishing operations, followed by hydration in a buffered saline solution, to provide a stable, shaped eye bandage having uniform physical properties.

2. Description of the Prior Art

Contact lens compositions prepared from polymeric materials are known:

U.S. Pat. No. 3,220,960 discloses hydrophilic copolymers of a monoester of acrylic or methacrylic acid with a diester of acrylic or methacrylic acid having desirable optical and physiological properties. U.S. Pat. No. 3,408,429 and 3,496,524 disclose various aspects of contrifugal casting and manufacturing soft contact lenses using the hydrophilic copolymers described in U.S. Pat. No. 3,220,960.

U.S. Pat. No. 3,700,761 discloses compositions comprising of HEMA (hydroxy-ethyl methacrylate) or HPMA (hydroxy-propyl methacrylate) with PVP in proportions of 20-45%, with up to 1% MA and about 0.2% EDMA. A two stage polymerization process, followed by radiation curing, cutting and hydration provides the finished contact lens.

U.S. Pat. No. 3,816,571, 3,822,196, and 3,829,329 disclose various aspects of the fabrication procedures generally described in aforementioned U.S. Pat. No. 3,700,761.

U.S. Pat. No. 3,807,398 discloses improvements in the U.S. Pat. No. 3,700,761 by careful regulation of ingredient concentrations and the addition of certain polymerization inhibitors to stabilize the HEMA. In addition, the polymeric composition is cast in a curved break away mold which eliminates the need for grinding the cast surface of the lens.

SUMMARY OF THE INVENTION

A dimensionally stable composition suitable for use in preparing a corrective hydrated lens or an eye bandage is obtained by utilizing from 0 to 4 ppm of HQ polymerization inhibitor and from 50 to 250 ppm of MEHQ polymerization inhibitor, based on the amount of HEMA monomer, in the polymerization mix; initiating the polymerization with a low temperature, free radical initiator; de-gassing the polymerization mix prior to polymerization to remove substantially all oxygen; and conducting the initial polymerization reaction from 23° C to 30° C for 16 to 36 hours during which time the reaction exotherm is carefully controlled. A closed casting mold, lined with a polyester film material, is utilized for polymerizing and shaping the composition. The polymeric composition obtained may be cut, machined and polished to obtain a shaped eye bandage which is then hydrated in a buffered saline solution maintained at a pH of 7.0 to 7.1.

The mold of this invention is particularly suitable for polymerizing materials in the shape of a rod or the like which is to be later machined into articles such as contact lenses. Examples of materials for which the mold is particularly suited for use include polymers and mixtures of polymers of methyl methacrylate, hydroxyethylmethacrylate and polycarbonates such as poly(-diethylene glycol bis-allyl carbonate) or CR39 (Trademark of PPG Industries, Pittsburgh, Pa.). The mold of the present invention may be used for casting rods of any polymer of a prepolymer whose polymerization is inhibited by the presence of oxygen. One advantage of the mold of the present invention is the ease of removing the polymer rod from the mold after polymerization. Another advantage of the mold, when used according to the present invention, is the strain-free, dimensionally-stable characteristics of the polymer product. These characteristics are especially important if the ultimate products are shaped eye bandages.

DESCRIPTION OF THE PARTICULAR EMBODIMENTS

It has now been found that a stable eye bandage composition, suitable for precision cutting and shaping, followed by hydration in a buffered saline solution, can be obtained by carefully controlling the formulation ingredients, the polymerization processes and the molding techniques. The stable eye bandage product obtained has been found to be predictable and reproducible both in the wet and dry states. Additionally, the improved eye bandage remains stable indefinitely without change in critical dimensions.

Specifically, it has been found that while a polymerization inhibitor is needed, the hydroquinone inhibitor adversely affects the HEMA polymerization as well as the polyHEMA/PVP graft polymerization reaction. Therefore, no more than 4 ppm, based on the amount of HEMA, of hydroquinone should be present for optimum polymer formation. The methyl ether of hydroquinone, which does not exhibit the disadvantages of hydroquinone, has been found to be effective at levels of 50 to 250 ppm, based on the amount of HEMA, for inhibiting polymerization prior to the addition of the polymerization initiator.

Additionally, it has been found that only a low temperature free radical polymerization initiator is necessary for complete polymerization. Prior art processes required an additional medium temperature free radical polymerization initiators. According to the teachings of this invention, initiators such as acetyl peroxide, disecondary-butyl peroxydicarbonate, cyclohexanone peroxide and the like, which operate between 23° C to 80° C, are suitable to initiate polymerization, and no additional initiators are necessary. Among these, disecondary-butyl peroxydicarbonate, used at a level of .02% by weight, based on the weight of the polymerization mix is preferred.

The following formulation is suitable for preparing the dimensionally stable eye bandage composition of this invention:

| Ingredients | Amount |
|---|---|
| HEMA | 67.2% to 79.3% |
| PVP | 14.25% to 35% |
| MA | 0.1% to 2.5% |
| EDMA | 0.1% to 4.04% |
| Initiator | 0.005% to 0.2% |
| Water | 0.1% to 5.0% |
| HQ | 0 to 4.0 ppm parts of HEMA |
| MEHQ | 50 to 250 ppm parts of HEMA |

A preferred formulation, corrected for impurities, for preparing the improved eye bandage composition of this invention contains:

| Ingredients | Amount |
|---|---|
| HEMA | 75.7% |
| PVP | 19.4% |
| MA | 1.2% |
| EDMA | 0.54% |
| Initiator | 0.02% |
| Water | 3% |
| HQ | less than 4 ppm parts HEMA |
| MEHQ | 100–200 ppm parts HEMA |

Water in the above formulations is not added as such: it is inherently present in ingredients such as HEMA and PVP, together with moisture absorbed from the atmosphere prior to and subsequent to mixing and fabricating operations.

The above formulation is polymerized according to the improved process of this invention. Specifically, the formulation is de-gassed prior to polymerization to remove substantially all oxygen. Vacuum de-gassing, using known techniques, has been found effective when performed on the polymerization mix in the casting mold, just prior to polymerization. Preferably, the de-gassing operation is performed twice: once on the polymerization mix, after the addition of the polymerization initiator and again after the polymerization mix has been poured into the casting mold. After the second de-gassing, the mold is back-flushed with an inert gas such as dry nitrogen, and the casting mold is immediately closed to prevent further contamination with atmospheric oxygen. The presence of oxygen and the hydroquinone polymerization inhibitor have been found to seriously inhibit both the HEMA polymerization and the polyHEMA/PVP graft polymerization reactions. Therefore, by removing substantially all oxygen, including atmospheric oxygen, before and during polymerization, and by limiting the amount of hydroquinone to less than four parts per million, based on the amount of HEMA, bulk polymerization of HEMA will take place at low temperatures.

High exothermic activity during the low temperature polymerization reaction has also been found to adversely affect the physical characteristics and uniform properties of the polymer formed. Thus, while the polymerization reaction may be conducted at temperatures of from 23° C to 30° C, with adjustments in amounts of polymerization initiator, the temperature selected is controlled so that the reaction exotherm does not vary more than about 4° C, preferably 2° C during the 16–36 hour low temperature polymerization period. This may be accomplished by placing the closed casting mold containing the de-gassed polymerization mix in a medium which will continuously absorb the heat of the polymerization reaction. Preferably, this low temperature polymerization reaction is conducted by placing the mold in a constant temperature water bath maintained at 25°± 0.1° C. for about 24 hours. The closed mold is positioned in the bath so as to prevent contamination of the polymerization mix with water from the bath. Most of the HEMA is polymerized during this stage.

Next, the mold is removed from the heat absorbing medium and heated to a temperature of from about 40° C. to about 80° C. for from two to six hours in order to complete polymerization of any remaining HEMA monomer. Preferably, the closed mold is placed in an oven maintained at a temperature of about 70° C. for approximately 2 hours.

The completion of the graft polymerization of the PVP and the HEMA polymer is achieved by heating the polymerized HEMA and the PVP to a temperature from about 105° to 125° C. for from 24 to 36 hours. This reaction can be performed after the reactants have been removed from the mold since the polymerized HEMA is in the solid state. Preferably, as will be explained below, the reactants, encased in a polyester film material, are heated in an oven maintained at 110° C. for 24 hours.

Substantially all bulk and graft polymerization reactions are completed after the above-mentioned heat treatment. An additional polymerization initiator operable at medium to high temperatures is not required for curing. This is particularly advantageous since the benzoyl peroxide initiator used to complete HEMA polymerization in prior processes has been found to react with hydroquinone present in the polymerization mix to form benzoquinone, which exerts a much more powerful inhibiting effect than HQ on the polymerization reactions taking place. Using the improved formulation and polymerization process of this invention, no further initiator or post-curing steps are necessary. A cured polymeric product having substantially uniform physical properties is obtained wihout irradiation or treatment with hydrogen peroxide previously required to achieve complete cure.

The casting and molding methods used to prepare the eye bandage compositions have also been found to be critcal. For casting and molding, an oxygen absorbant mold tube having an end plug and a cap as a convenient closure for one end of the mold tube is used. A split ring or similar device is useful to provide a support for the mold during suspension in a temperature-controlled fluid bath. A polyester film coil is used to line the interior surface of the mold tube. The polyester film is coiled prior to insertion into the mold tube. Mold materials, which are critical to the practice of the present invention, include an oxygen absorbent material for the mold tube and an oxygen non-absorbent polyester film as the lining for the tube. The oxygen absorbent properties of polytetrafluoroethylene are well known and tubes of the type illustrated are commercially available made of Teflon (Trademark of E.I. duPont de Nemours, Wilmington, Deleware). A suitable oxygen non-absorbent material for the lining is exemplified by polyester films, especially the polyethylene terephthalate films marketed commercially as Mylar (a Trademark of E.I. duPont de Nemours, Wilmington, Deleware). After the mold is filled with the prepolymer mix, the other end of the mold tube is closed with a plug. Preferably, the mold plugs are also made of an oxygen non-absorbent polyester material.

The oxygen absorbent and non-absorbent properties of the mold and lining are particularly critical to the practice of the invention. These properties enables one to conduct the polymerization in the mold and remove the rod cast by polymerization therein without difficulty or damage to the rod or to the mold. The oxygen absorbent property of the mold tube prevents polymerization of the mix in contact therewith. Therefore, any prepolymer mix which leaks between layers of the coil or around the ends of the coil and contacts the mold tube does not harden and/or bond either the rod and/or the polyester lining to the mold tube. Upon completion of the casting step it is therefore easy to remove the rod with the polyester film from the tube and subsequently unwind the coil from around the rod. The mold size and shape is not critical and may be varied to accommodate available fabricating equipment. Eye bandage "buttons" or "rods" of polymerized stock from which the individual eye bandages can be cut may be obtained according to the molding process of this invention. In a preferred embodiment, tubular, polytetrafluoroethylene casting molds of from 330–380 millimeters in length and having inside diameter of approximately 15.8 millimeters are used. This open-ended rod-shaped mold is lined with the polyester film material and closed with top and bottom cap plugs at various stages during the molding operation. For example, after the polyester lining is in place, the bottom cap plug is affixed and the polymerization mix is added to the mold; the polymerization mix is de-gassed, the system is back-flushed with an inert gas, and the top cap plug is affixed immediately to prevent contamination with atmospheric oxygen. The polymerization reaction is then conducted as described above. Removal of the polymerized mass from the mold is facilitated by the presence of the polyester film lining: the top and bottom cap plugs are removed, and the polyester encased self-supporting polymerized mass can be removed by exerting a small amount of pressure on either end of the polymerized mass within the mold. The mold may be re-used after a relatively simple cleaning operation. The self-supported polymerized mass within the polyester film lining is heated at 110° C. as described above, to complete the graft polymerization reaction. The polyester film is then removed from the polymerized rod and discarded. The cured rod stock thus obtained can be cut and machined easily on existing contact lens equipment.

Techniques for cutting, machining, and polishing the eye bandage composition prepared as described above are known in the art and are generally described by Mullen in U.S. Pat. No. 2,330,837, Feinbloom in U.S. Pat. No. 3,227,507, O'Driscoll et al. in U.S. Pat. No. 3,700,761 and by Gruzca in U.S. Pat. No. 3,807,398. Aforementioned U.S. Pat. Nos. 2,300,837, 3,227,507, 3,700,761 and 3,807,398 are incorporated herein by reference.

Individual eye bandage compositions which have been cut, machined and polished are hydrated in a buffered saline solution according to the process of this invention. It has been found that the pH of the hydration operation is critical and must be conducted at a pH of from about 7.0 to about 7.1. A physiological saline solution (0.85% to 0.9% sodium chloride) is buffered with an ophthamalogically acceptable buffer which will not interfere with the optical qualities of the eye bandage, to maintain the pH of from about 7.0 to about 7.1. Suitably, a monobasic sodium phosphate/dibasic sodium phosphate buffer system is used for this purpose.

Hydration is conducted in the above-described solution for a time sufficient to remove water-soluble extractables from the eye bandage composition and establish a constant set of hydration parameters. It has been found that the extractable levels as low as from 2% to 3% are obtained using the improved formulating, polymerizing and molding processes of this invention. Thus, hydration time is greatly reduced. Significantly, it has been found that by using a 0.9% saline solution, buffered to maintain a pH of from about 7.0 to 7.1, the equilibration of the eye bandage composition of this invention is achieved in from five to seven days. In order to insure complete equilibration, the hydration process is preferably conducted for 7 days. Equilibrating and hydrating processes used for prior art eye bandage compositions frequently required a 30 day treatment period and numerous processing steps. By reducing the extractable levels in the polymeric composition and using the one-step hydration process of this invention, an improved hydrated eye bandage composition is obtained in a much shorter period of time.

The hydrated compositions of this invention may also be adapted for use as an eye bandage for dispensing medication.

As described by O'Driscoll et al. in U.S. Pat. No. 3,700,761 and by Gruzca in U.S. Pat. No. 3,807,398, water soluble medicaments can be added to the contact lens by dissolving the medicaments in water and adding 5% of the aqueous solution of the medicament to the HEMA monomer prior to polymerization. Especially useful eye bandages are prepared in this manner. The additional water in the polymerization mix makes the lens, after hydration, spongy, and the medicament present is released with greater facility. Opthalmologically acceptable medicaments suitable for this purpose are known and include corticosteroids, sulfonamides, disinfectants, antiseptics, penicillin, pilocarpine, belladonna, dibenzyline, hydergine, methacholine, carbachol, bethanechol and the like.

In preparing the compositions of this invention for use as eye bandages to release medicament, formulating, polymerizing, molding and hydrating procedures may be varied within the above-mentioned critical limits to accommodate properties of the medicament being used. For example, heating temperature and times may be lowered to avoid drug decomposition. Additionally, drug dosages for the eye which require a great degree of precision can be administered using the shaped eye bandage of this invention. In such instances, it may be preferable to set up a fountain solution of the drug in saline and drop this solution onto the eye bandage to deliver the dosage to the eye at a constant rate for a controlled time.

In all of the aforementioned descriptions of the eye bandage compositions of this invention, the abbreviations used are defined as follows:
HEMA — Hydroxyethyl Methacrylate
PVP — Poly-N-Vinyl Pyrrolidone
EDMA — Ethylene Glycol Dimethacrylate
MA — Methacrylic Acid
ppm — parts per million
HQ — Hydroquinone
MEHQ — Methyl Ether of Hydroquinone Thus, according to the teachings of this invention there is obtained a dimensionally stable composition suitable for use in preparing a corrective hydrated lens or an eye bandage having uniform physical properties in both the wet and dry states, together with the required strength and toughness for such lens compositions. The improved eye bandage composition of this invention is obtained by critically selecting formulation ingredients and carefully controlling polymerization, molding and hydration processes.

In order to further illustrate this invention, the following examples are provided:

EXAMPLE I

Preparation of A Shaped Eye Bandage

665 Grams of HEMA, 170 grams of PVP, 10.2 grams of MA, 4.76 grams of EDMA, 0.001 grams of HQ, and 0.0065 grams of MEHQ are placed in a glass container which is closed with a Mylar lined cap. The bottle is shaken for 10 to 15 seconds to break up the PVP and then placed on a laboratory rolling mill for 1½ to 2 hours to complete solvation of the PVP. The premix is removed from the glass container and pressure filtered through a Seitz or pall filtering apparatus with 7 to 30 micron filer paper. The filtered premix is refrigerated at 0° to 4° C.

0.17 Grams of disecondary-butyl peroxydicarbonate is added to the cold premix and the initiator-containing mix is then vigorously shaken for ten seconds, after which it is placed on a rolling mill for 30 minutes. The mix is then transferred into a suitable container and de-gassed for 10 to 15 minutes at 1–50 mm of reduced pressure. When releasing the vacuum, the chamber is back-flushed with dry nitrogen.

A 5 mil Mylar sheeting is cut into strips and rolled onto a steel rod having a diameter of 12.7 mm and inserted into a Teflon casting tube 330 millimeters long having an inside diameter of 15.8 millimeters and an outside diameter of 19.0 millimeters. The liner is wiped clean of gross particulate matter prior to insertion and the tube is blown out with dry nitrogen from both ends following the insertion of the Mylar liner. The bottom cap plug, which has been soaked in acetone for 24 hours prior to use, is affixed to the casting tube and the polymerization mix is poured into place. The casting tube containing the polymerization mix is de-gassed in a vacuum chamber for 20–40 minutes at 1–50 mm of reduced pressure. The system is back-flushed with dry nitrogen as the vacuum is released. The casting tube is removed from the vacuum chamber and the top cap plug is affixed tightly immediately.

The closed casting tube is placed in a rack in a constant temperature water bath maintained at 25° C ± 0.1° C for 20 hours, with the closed casting tube positioned so as to prevent contamination of the polymerization mix with water from the water baths. The casting tube is then transferred to an air circulating oven set at 70° C ± 1° C for 2 hours. The casting tube is then taken out of the oven and the casting is taken out of the tube by removing the cap plugs and then using a steel or aluminum poking rod. The casting, encased in the Mylar lining, slides easily out of the tube. The liner is not removed and the encased casting is placed in an air circulating oven, set at 110° C ± 1° C for 24 hours.

The Mylar liner is then removed; the cast rods are visually inspected and stored in sealed glass or Mylar containers until needed. The empty casting tubes are cleaned by soaking in water, rinsing and allowing to dry before reuse.

The hard polymerized cast rods are subjected to known machining, cutting and polishing techniques as described in U.S. Pat. Nos. 2,330,837, 3,227,507, 3,700,761, and 3,807,398, to form individual eye bandage compositions.

EXAMPLE II

Hydration of the Eye Bandage Composition

A buffered physiological saline solution is prepared from 8.50 grams of reagent grade sodium chloride, 0.2545 grams monobasic sodium phosphate, 0.7006 grams dibasic sodium phosphate and distilled water, added to 1,000 ml. This buffered solution will maintain a pH of about 7.1. The individual eye bandage compositions of Example I are hydrated in this solution at 22° C to 25° C for 7 days. Thereafter, the hydrated eye bandage compositions are stored indefinitely in saline solution.

We claim:

1. A dimensionally stable shaped eye bandage for medicament delivery which can be cut and shaped in the dry form and thereafter hydrated in a buffered saline solution to form a bandage having from about 45% to 65% water after hydration, said bandage in dry form consisting essentially of polymerized random graft copolymers containing from about 67.2% to about 79.3% HEMA; from about 14.25% to about 35% PVP; from about 0.1% to about 4.04% EDMA; from about 0.1% to about 2.5% MA; from about 0.1% to about 5.0% water; from about 0 to about 4 ppm, based on the weight of HEMA monomer, of HQ inhibitor; and from about 50 to 250 ppm, based on the weight of HEMA monomer, of MEHQ inhibitor; said composition having been polymerized using only a low temperature polymerization initiator, with substantially all the oxygen having been removed from the polymerization mix prior to and during the polymerization reaction; the initial polymerization reaction being conducted at from 23° C to about 30° C., for from about 16 to about 30 hours, with the heat of the reaction continuously absorbed to control the reaction exotherm.

2. A shaped eye bandage according to claim 1 wherein about 75.7% HEMA, about 19.4% PVP, about 0.54% EDMA, about 1.2% MA, about 3.0% water; from 0 to 4 ppm, based on the weight of the HEMA monomer, of HQ inhibitor, and from about 100 to 200 ppm, based on the weight of HEMA monomer, of MEHQ inhibitor are present in the substantially dry form of the contact lens composition.

3. A shaped eye bandage according to claim 1 wherein about 75.7% HEMA, about 19.4% PVP, about 0.54% EDMA, about 1.2% MA, about 3.0% water, and from 100 to 200 ppm, based on the weight of HEMA monomer, of MEHQ inhibitor are present in the substantially dry form of the contact lens composition.

4. A shaped eye bandage according to claim 2 wherein the initial polymerization reaction is conducted at about 24° C to 26° C for about 20 hours in a constant temperature water bath.

5. A shaped eye bandage according to claim 2 wherein the eye bandage is hydrated in a 0.85% to 0.9% saline solution, buffered to maintain a pH of from about 7.0 to 7.1.

* * * * *